US012690839B2

(12) United States Patent

Pickering et al.

(10) Patent No.: US 12,690,839 B2

(45) Date of Patent: Jul. 28, 2026

(54) DEVICES, SYSTEMS, AND METHODS FOR TRANSVAGINAL, ULTRASOUND GUIDED HYSTEROSCOPIC SURGICAL PROCEDURES

(71) Applicant: Covidien LP, Mansfield, MA (US)

(72) Inventors: Chad A. Pickering, Woburn, MA (US); Arvind Rajagopalan Mohan, Dracut, MA (US); Scott J. Prior, Branford, CT (US); Kolby A. Faria, Lowell, MA (US)

(73) Assignee: Covidien LP, Mansfield, MA (US)

( * ) Notice: Subject to any disclaimer, the term of this patent is extended or adjusted under 35 U.S.C. 154(b) by 111 days.

(21) Appl. No.: 18/499,156

(22) Filed: Oct. 31, 2023

(65) Prior Publication Data

US 2024/0341722 A1 Oct. 17, 2024

Related U.S. Application Data

(60) Provisional application No. 63/459,359, filed on Apr. 14, 2023.

(51) Int. Cl.
*A61B 8/00* (2006.01)
*A61B 8/12* (2006.01)

(52) U.S. Cl.
CPC .............. *A61B 8/12* (2013.01); *A61B 8/4209* (2013.01); *A61B 8/4466* (2013.01)

(58) Field of Classification Search
CPC ....... A61B 8/12; A61B 8/4209; A61B 8/4466; A61B 1/00066; A61B 1/015; A61B 1/07; A61B 17/32002; A61B 2017/4216; A61B
2090/034; A61B 2090/306; A61B 2090/378; A61B 1/0014; A61B 8/445; A61B 1/018; A61B 1/303; A61B 8/42; A61B 8/4494
See application file for complete search history.

(56) References Cited

U.S. PATENT DOCUMENTS

| | | |
|---|---|---|
| 5,166,787 A | 11/1992 | Irion |
| 5,351,678 A | 10/1994 | Clayton |
| 5,935,057 A | 8/1999 | Lichtman et al. |
| 6,156,006 A | 12/2000 | Brosens et al. |
| 6,174,307 B1 | 1/2001 | Daniel et al. |

(Continued)

OTHER PUBLICATIONS

Extended European Search Report issued in corresponding European Application No. 24169978.4 dated Jul. 4, 2024, 9 pages.

*Primary Examiner* — Michael J Carey
*Assistant Examiner* — Zainab Mohammed Aldarraji
(74) *Attorney, Agent, or Firm* — Carter, DeLuca & Farrell, LLP

(57) ABSTRACT

A transvaginal ultrasound device includes a collar, a body, and an ultrasound sensor assembly. The collar defines a longitudinal lumen configured to receive a shaft for slidably positioning the collar about the shaft. The body depends from the collar and protrudes distally relative to the collar. The ultrasound sensor assembly is disposed within the body and configured for ultrasound imaging. The collar and the body are configured for full insertion through a vaginal introitus and into a vaginal canal of a human patient for positioning the longitudinal lumen of the collar in substantial alignment with a cervix of the human patient to enable the shaft to extend through the cervix and into a uterus of the human patient.

20 Claims, 12 Drawing Sheets

(56)                    References Cited

U.S. PATENT DOCUMENTS

| | | | |
|---|---|---|---|
| 6,210,330 | B1 | 4/2001 | Tepper |
| 6,884,219 | B1 | 4/2005 | Pruter |
| 6,896,657 | B2 | 5/2005 | Willis |
| 6,936,048 | B2 | 8/2005 | Hurst |
| 6,960,166 | B1 | 11/2005 | Wong et al. |
| 7,517,346 | B2 | 4/2009 | Sloan et al. |
| 7,520,856 | B2 | 4/2009 | Vaezy et al. |
| 7,591,785 | B2 | 9/2009 | Wendlandt et al. |
| 7,621,869 | B2 | 11/2009 | Ratnakar |
| 7,815,571 | B2 | 10/2010 | Deckman et al. |
| 7,874,986 | B2 | 1/2011 | Deckman et al. |
| 7,918,795 | B2 | 4/2011 | Grossman |
| 8,088,072 | B2 | 1/2012 | Munrow et al. |
| 8,206,300 | B2 | 6/2012 | Deckman et al. |
| 8,262,574 | B2 | 9/2012 | Placek et al. |
| 8,262,577 | B2 | 9/2012 | Munrow et al. |
| 8,298,145 | B2 | 10/2012 | Deckman et al. |
| 8,506,485 | B2 | 8/2013 | Deckman et al. |
| 8,992,427 | B2 | 3/2015 | Munrow et al. |
| 9,357,977 | B2 | 6/2016 | Grossman |
| 9,517,047 | B2 | 12/2016 | Grossman |
| 9,808,310 | B2 | 11/2017 | Grossman |
| 9,861,336 | B2 | 1/2018 | Munrow et al. |
| 9,987,080 | B2 | 6/2018 | Grossman |
| 10,058,342 | B2 | 8/2018 | Deckman et al. |
| 10,182,862 | B2 | 1/2019 | Grossman |
| 10,321,951 | B2 | 6/2019 | Placek et al. |
| 10,595,819 | B2 | 3/2020 | Deckman et al. |
| 10,610,197 | B2 | 4/2020 | Deckman et al. |
| 10,750,939 | B2 | 8/2020 | Begg |
| 2004/0153105 | A1 | 8/2004 | Burbank et al. |
| 2004/0158262 | A1 | 8/2004 | Burbank et al. |
| 2004/0181152 | A1 | 9/2004 | Zhang et al. |
| 2005/0203399 | A1 | 9/2005 | Vaezy et al. |
| 2005/0234294 | A1 | 10/2005 | Saadat et al. |
| 2005/0272975 | A1 | 12/2005 | McWeeney et al. |
| 2006/0004410 | A1 | 1/2006 | Nobis et al. |
| 2006/0189972 | A1 | 8/2006 | Grossman |
| 2007/0112272 | A1 | 5/2007 | Park et al. |
| 2007/0213749 | A1 | 9/2007 | Kogasaka |
| 2007/0244353 | A1 | 10/2007 | Larsen |
| 2007/0249939 | A1 | 10/2007 | Gerbi et al. |
| 2008/0287916 | A1 | 11/2008 | Agmon |
| 2009/0259097 | A1 | 10/2009 | Thompson |
| 2009/0318758 | A1 | 12/2009 | Farr et al. |
| 2011/0160535 | A1 | 6/2011 | Bayer et al. |
| 2012/0116248 | A1 | 5/2012 | Mcweeney et al. |
| 2012/0245416 | A1 | 9/2012 | Viola |
| 2013/0046137 | A1 | 2/2013 | Zhao et al. |
| 2014/0100558 | A1 | 4/2014 | Schmitz et al. |
| 2014/0180001 | A1 | 6/2014 | Grunberg et al. |
| 2014/0228875 | A1 | 8/2014 | Saadat |
| 2014/0276081 | A1 | 9/2014 | Tegels |
| 2015/0018685 | A1* | 1/2015 | Barker ................. A61B 8/4218 |
| | | | 600/459 |
| 2015/0201964 | A1 | 7/2015 | Murdeshwar et al. |
| 2016/0287210 | A1 | 10/2016 | Chumo et al. |
| 2017/0245838 | A1 | 8/2017 | Munrow et al. |
| 2017/0245891 | A1 | 8/2017 | Munrow et al. |
| 2017/0290626 | A1 | 10/2017 | Deckman et al. |
| 2017/0290627 | A1 | 10/2017 | Deckman et al. |
| 2017/0319174 | A1 | 11/2017 | Hill et al. |
| 2017/0340308 | A1 | 11/2017 | Cermak et al. |
| 2018/0008237 | A1 | 1/2018 | Venkataraman et al. |
| 2018/0042572 | A1 | 2/2018 | Munrow et al. |
| 2018/0078303 | A1 | 3/2018 | Grossman |
| 2018/0132927 | A1 | 5/2018 | Chen et al. |
| 2018/0206712 | A1 | 7/2018 | Begg |
| 2018/0318026 | A1 | 11/2018 | Placek |
| 2019/0142370 | A1 | 5/2019 | Roy et al. |
| 2019/0192217 | A1 | 6/2019 | Grossman |
| 2019/0262080 | A1 | 8/2019 | Hammudi et al. |
| 2019/0269456 | A1 | 9/2019 | Placek et al. |
| 2019/0350648 | A1 | 11/2019 | Owens et al. |
| 2020/0229892 | A1 | 7/2020 | Munrow et al. |
| 2020/0275975 | A1 | 9/2020 | Chen |
| 2021/0204910 | A1* | 7/2021 | Begg ................... A61B 8/0841 |
| 2022/0401071 | A1 | 12/2022 | Prior |

* cited by examiner

DEVICES, SYSTEMS, AND METHODS FOR TRANSVAGINAL, ULTRASOUND GUIDED HYSTEROSCOPIC SURGICAL PROCEDURES

CROSS-REFERENCE TO RELATED APPLICATION

This application claims the benefit of, and priority to, U.S. Provisional Patent Application No. 63/459,359, filed on Apr. 14, 2023, the entire contents of which are hereby incorporated herein by reference.

FIELD

The present disclosure relates to hysteroscopy and, more particularly, to devices, systems, and methods for transvaginal, ultrasound guided hysteroscopic surgical procedures.

BACKGROUND

Transvaginal hysteroscopy includes both intrauterine procedures, e.g., procedures performed within the uterine cavity, and intramural procedures, e.g., procedures performed within the uterine wall. Intrauterine procedures may require different approaches and/or instruments as compared to intramural procedures, and vice versa. Even within the same category, hysteroscopic procedures may require different approaches and/or instruments depending upon, for example, the procedure to be performed, patient anatomy, technique utilized, and/or other considerations.

SUMMARY

As used herein, the term "distal" refers to the portion that is being described which is farther from a user, while the term "proximal" refers to the portion that is being described which is closer to a user. To the extent consistent, any or all of the aspects detailed herein may be used in conjunction with any or all of the other aspects detailed herein.

Provided in accordance with aspects of the present disclosure is a transvaginal ultrasound device including a collar, a body, and an ultrasound sensor assembly. The collar defines a longitudinal lumen configured to receive a shaft for slidably positioning the collar about the shaft. The body depends from the collar and protrudes distally relative to the collar. The ultrasound sensor assembly is disposed within the body and configured for ultrasound imaging. The collar and the body are configured for full insertion through a vaginal introitus and into a vaginal canal of a human patient for positioning the longitudinal lumen of the collar in substantial alignment with a cervix of the human patient to enable the shaft to extend through the cervix and into a uterus of the human patient.

In an aspect of the present disclosure, the device further includes a locking mechanism configured to releasably lock the collar about the shaft to at least one of slidably or rotationally fix the collar relative to the shaft. In such aspects, the locking mechanism may include a locking drive assembly configured to transition the locking mechanism between a locked condition and an unlocked condition.

In another aspect of the present disclosure, the body is fixed relative to the collar. Alternatively, the body is movable relative to the collar. More specifically, the body may be rotatable, slidable, and/or pivotable relative to the collar.

In another aspect of the present disclosure, the device further includes a drive assembly configured to move the body relative to the collar.

A hysteroscopic surgical system provided in accordance with the present disclosure includes a hysteroscope including a handle and a shaft extending distally from the handle, and an ultrasound device. The ultrasound device includes a collar defining a longitudinal lumen configured to receive the shaft for slidably positioning the collar about the shaft, a body depending from the collar and protruding distally relative to the collar, and an ultrasound sensor assembly disposed within the body. The ultrasound sensor assembly is configured for ultrasound imaging. The collar and the body are configured for positioning within a vaginal canal of a human patient for positioning the longitudinal lumen of the collar in substantial alignment with a cervix of the human patient to enable the shaft to extend through the cervix and into a uterus of the human patient.

In an aspect of the present disclosure, the shaft of the hysteroscope includes a first portion defining a first diameter and a second portion defining a second diameter greater than the first diameter. In such aspects, the longitudinal lumen of the collar may define a third diameter greater than the first diameter but less than the second diameter to enable slidable positioning the collar about the first portion of the shaft and inhibit sliding of the collar onto the second portion of the shaft.

In another aspect of the present disclosure, the hysteroscopic surgical system further includes a spacer configured for positioning about the shaft of the hysteroscope proximally of the collar. The spacer is configured to define an extent of distal insertion of the shaft of the hysteroscope through the collar.

In still another aspect of the present disclosure, the spacer is configured for positioning about the shaft of the hysteroscope between the collar and a transition defined along the shaft.

In yet another aspect of the present disclosure, the hysteroscopic surgical system further includes a locking mechanism configured to releasably lock the collar about the shaft to at least one of slidably or rotationally fix the collar relative to the shaft. In such aspects, the locking mechanism may include a locking drive assembly configured to transition the locking mechanism between a locked condition and an unlocked condition.

In still yet another aspect of the present disclosure, the body is fixed relative to the collar. Alternatively, the body is movable relative to the collar. For example the body may be rotatable, slidable, and/or pivotable relative to the collar.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
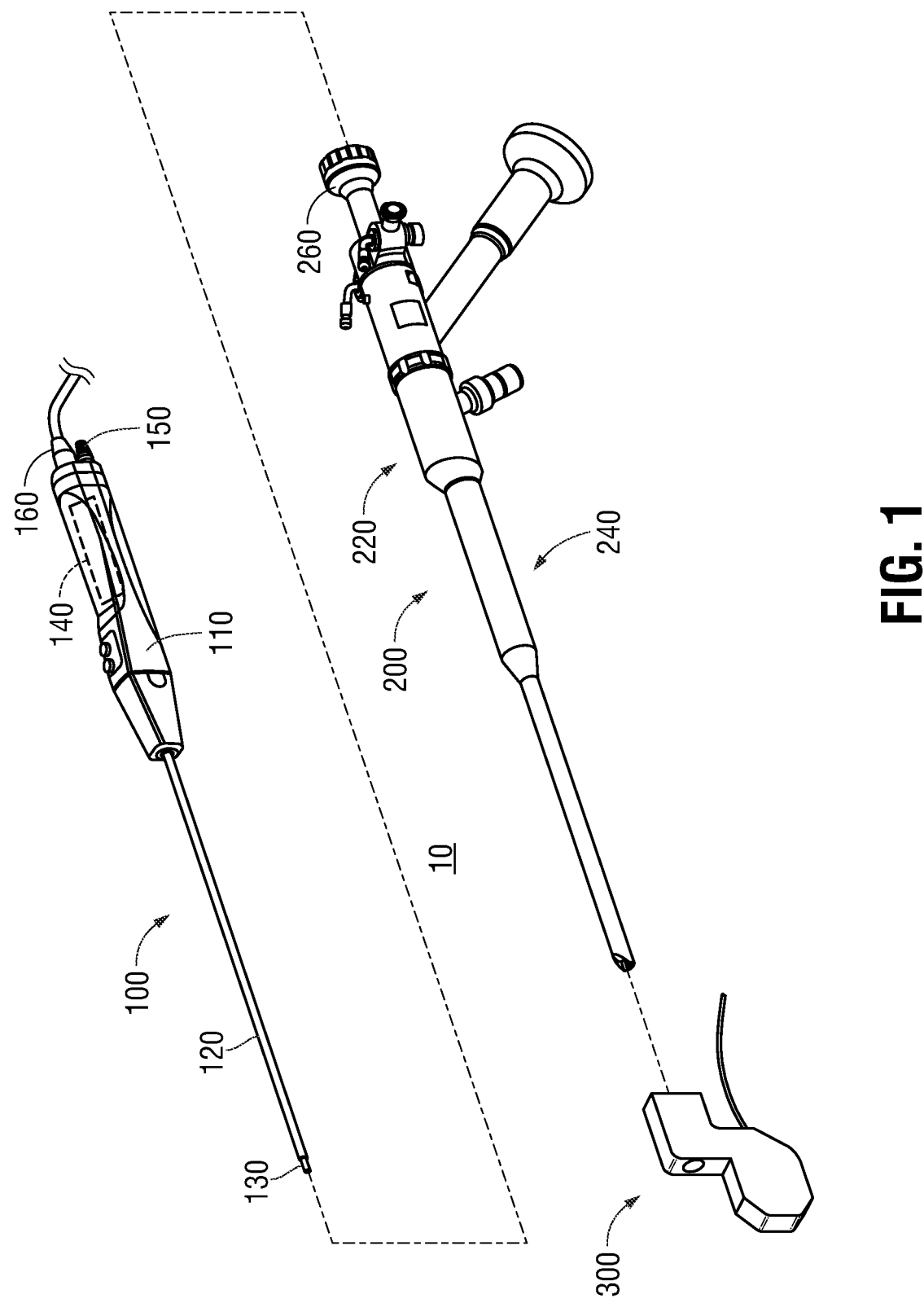
FIG. 1 is a perspective view of a hysteroscopic system provided in accordance with the present disclosure including a working device, a hysteroscope, and an ultrasound device.

Referring to FIG. 1, a hysteroscopic system provided in accordance with the present disclosure is shown generally identified by reference numeral 10 including a working device 100, e.g., a tissue resection device, an ablation device, a biopsy device, etc.; a hysteroscope 200; and an ultrasound device 300. Ultrasound device 300 is configured for transvaginal insertion into position adjacent to or in abutment with tissue surrounding the cervix of a patient (e.g., a human patient). Hysteroscope 200 is configured for insertion through ultrasound device 300 and the cervix into the uterus of the patient. Working device 100 is configured for insertion through hysteroscope 200 and into the uterus of the patient to perform a surgical procedure in the uterine cavity and/or within the uterine wall. Although described herein with respect to a hysteroscopic system for performing a surgical procedure within the uterus (e.g., within the uterine cavity and/or within the uterine wall), the aspects and features of the present disclosure are also applicable for use in other endoscopic procedures such as ultrasound guided endoscopic surgical procedures.

Working device 100, as noted above, may be a tissue resection device, an ablation device, a biopsy device, or other suitable working device configured for use on or within the uterus. With respect to a tissue resection device, for example, working device 100 includes a housing 110, a shaft 120, a cutting member 130, a drive mechanism 140, an outflow port 150, and a cable 160. Housing 110 houses drive mechanism 140 therein and functions as a handle to enable a user to grasp working device 100. Drive mechanism 140 includes a motor and is operably coupled to cutting member 130 to drive rotation and/or translation of cutting member 130 relative to shaft 120. Drive mechanism 140 is adapted to connect to a control unit (not shown) via cable 160 for powering and controlling the motor, although working device 100 may alternatively be battery powered or manually powered. A suction source (not shown) incorporated into the control unit (not shown), or any other suitable vacuum creating mechanism, may also be provided to facilitate withdrawal of fluid, tissue, and debris through working device 100 and outflow port 150.

Shaft 120 of working device 100 extends distally from housing 110 and, in aspects, is stationary relative to housing 110, although other configurations are also contemplated. Cutting member 130 extends through shaft 120 and is rotatable and/or translatable relative to shaft 120. More specifically, cutting member 130 is operably coupled to drive mechanism 140 for driving the rotation and/or translation of cutting member 130 relative to shaft 120 for cutting and removing tissue. A distal portion of cutting member 130 is exposed via an open distal end of shaft 120 (as shown) and/or a window defined through shaft 120.

In use of working device 100, upon activation, tissue is drawn into shaft 120 and/or cutting member 130. As tissue is drawn into shaft 120 and/or cutting member 130, the tissue is resected via the rotation and/or translation of cutting member 130 relative to shaft 120, thus enabling the resected tissue to be drawn proximally through shaft 120 and/or cutting member 130, along with fluid and debris. The resected tissue, fluid, and debris are drawn proximally through outflow port 150 and outflow tubing (not shown) and, ultimately, to one or more collection canisters of a fluid management system (not shown).

Figures 2A, 2B:
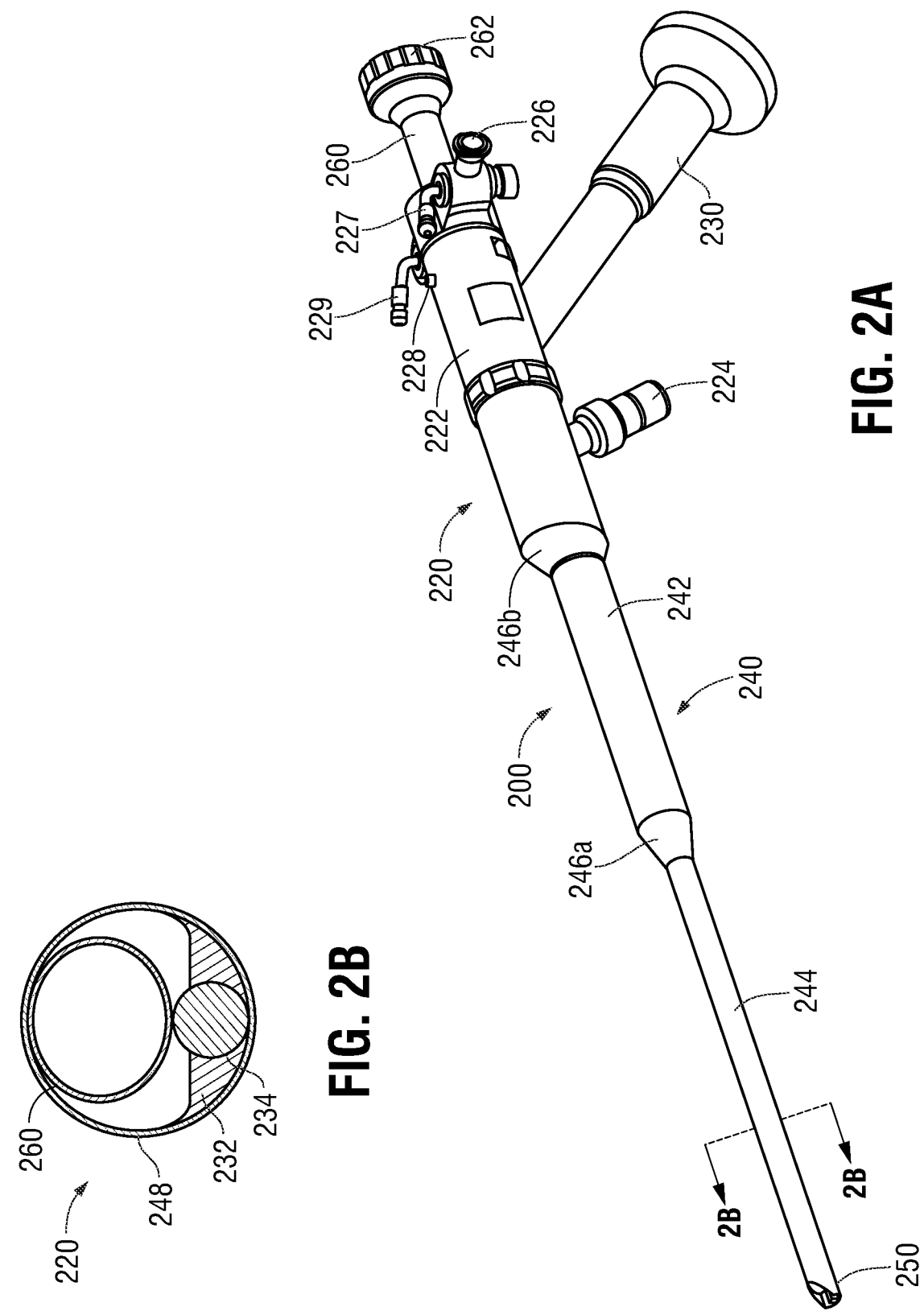
FIG. 2A is a perspective view of the hysteroscope of the hysteroscopic system of FIG. 1.
FIG. 2B is a transverse, cross-sectional view taken across section line "2B-2B" of FIG. 2A.

With additional reference to FIGS. 2A and 2B, hysteroscope 200 includes a handle 220, a shaft 240, and a removable outflow and/or instrument working channel 260. Handle 220 of hysteroscope 200 includes a housing 222, a light post 224, inflow and outflow ports 226, 228, respectively, inflow and outflow valves 227, 229, respectively, and an arm 230. Housing 222 defines a generally cylindrical-shaped configuration extending along a longitudinal axis defined by hysteroscope 200. Light post 224 extends from housing 222 and is configured to connect to a light source, e.g., to illuminate a distal end of shaft 240 via a plurality of fiber optic strands 232 (FIG. 2A) coupled to light post 224 and extending through shaft 240 to the distal end of shaft 240. Inflow and outflow ports 226, 228 enable connection of a fluid supply and a fluid collection container, respectively, to hysteroscope 200 to enable the inflow and outflow of fluid through shaft 240 to/from the internal surgical site, e.g., the uterus. Inflow and outflow valves 227, 229 enable the selective control of the fluid resistance through inflow and outflow ports 226, 228, respectively, thereby enabling control of fluid flow rate into and out of the internal surgical site. Arm 230 is configured to connect to an imaging device, e.g., a camera, to capture images received via optics 234 (FIG. 2A) extending through shaft 240 to the distal end of shaft 240 and, thus, enable display of a video image of the internal surgical site as captured by optics 234.

Shaft 240 of hysteroscope 200 extends distally from handle 220 along the longitudinal axis of hysteroscope 200 and includes including a proximal portion 242 having a first diameter, a distal portion 244 having a second, smaller diameter, and a first transition portion 246a disposed between proximal and distal portions 242, 244, respectively, and tapering from the first diameter to the second diameter to provide a transition between proximal and distal portions 242, 244, respectively. Further, a second transition portion 246*b* may be disposed between proximal portion 242 of shaft 240 and housing 222 of handle 220 to provide a transition tapering from the first diameter of proximal portion 242 of shaft 240 to a third diameter of housing 222 of handle 220 that is greater than the first diameter.

Distal portion 244 of shaft 240 of hysteroscope 200, defining a relatively small diameter, is configured for insertion transvaginally through the cervix and into the uterus. The relatively small diameter of distal portion 244 of shaft 240 reduces pain and discomfort for the patient and also provides increased flexibility compared to the relatively large diameter proximal portion 244, thus facilitating insertion through the cervix and into the uterus. Proximal portion 242 of shaft 240 of hysteroscope 200, defining a relatively large diameter, is configured for insertion transvaginally through the vaginal introitus and into the vaginal canal, but not through the cervix. The relatively large diameter proximal portion 242 provides increased structural support to shaft 240 of hysteroscope 200. Housing 222 of handle 220 of hysteroscope 220, defining the largest diameter, is configured to remain externally of the patient, to facilitate operating, manipulating, and/or supporting hysteroscope 200. Transition portion 246*a* of shaft 240 of hysteroscope 200 facilitates atraumatic insertion of relatively large diameter proximal portion 242 of shaft 240 of hysteroscope 200 through the vaginal introitus and into the vaginal canal and atraumatic contact with the cervix. Likewise, transition portion 246*b* of shaft 240 of hysteroscope 200 facilitates atraumatic contact with the vaginal introitus.

Shaft 240 includes, as noted above, the plurality of fiber optic strands 232 and optics 234 extending therethrough. Shaft 240 further includes a generally D-shaped inflow channel 248 extending therethrough. Inflow channel 248 fluidly communicates with inflow port 226. The plurality of fiber optic strands 232 and optics 234 extend through shaft 240 externally of inflow channel 248. Working channel 260 extends through inflow channel 248 and is removable therefrom, although in aspects, working channel 260 is integral with shaft 240. Working channel 260 functions as an outflow and/or instrument channel that fluidly communicates with outflow port 228. In aspects, channels 248, 260 may be reversed, e.g., wherein channel 248 is utilized for outflow and channel 260 is utilized for inflow. In aspects, working channel 260 includes a proximal seal assembly 262 configured to establish a seal about an instrument inserted through working channel 260.

Distal tip 250 of shaft 240 includes a partially-slanted configuration whereby the plurality of fiber optic strands 232 and optics 234 end at a perpendicular distal surface while the inflow channel 248 defines a slanted distal surface that is angled proximally from the distal surface of the plurality of fiber optic strands 232 and optics 234.

Figure 3:
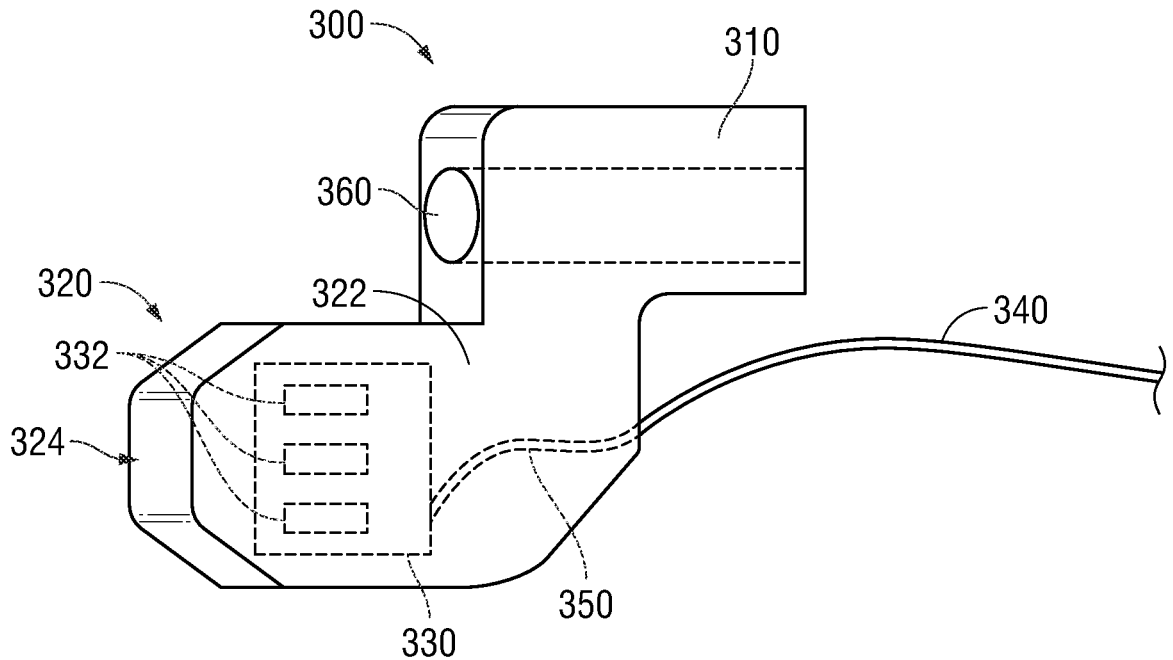
FIG. 3 is a perspective view of the ultrasound device of the hysteroscopic system of FIG. 1.
Figure 4:
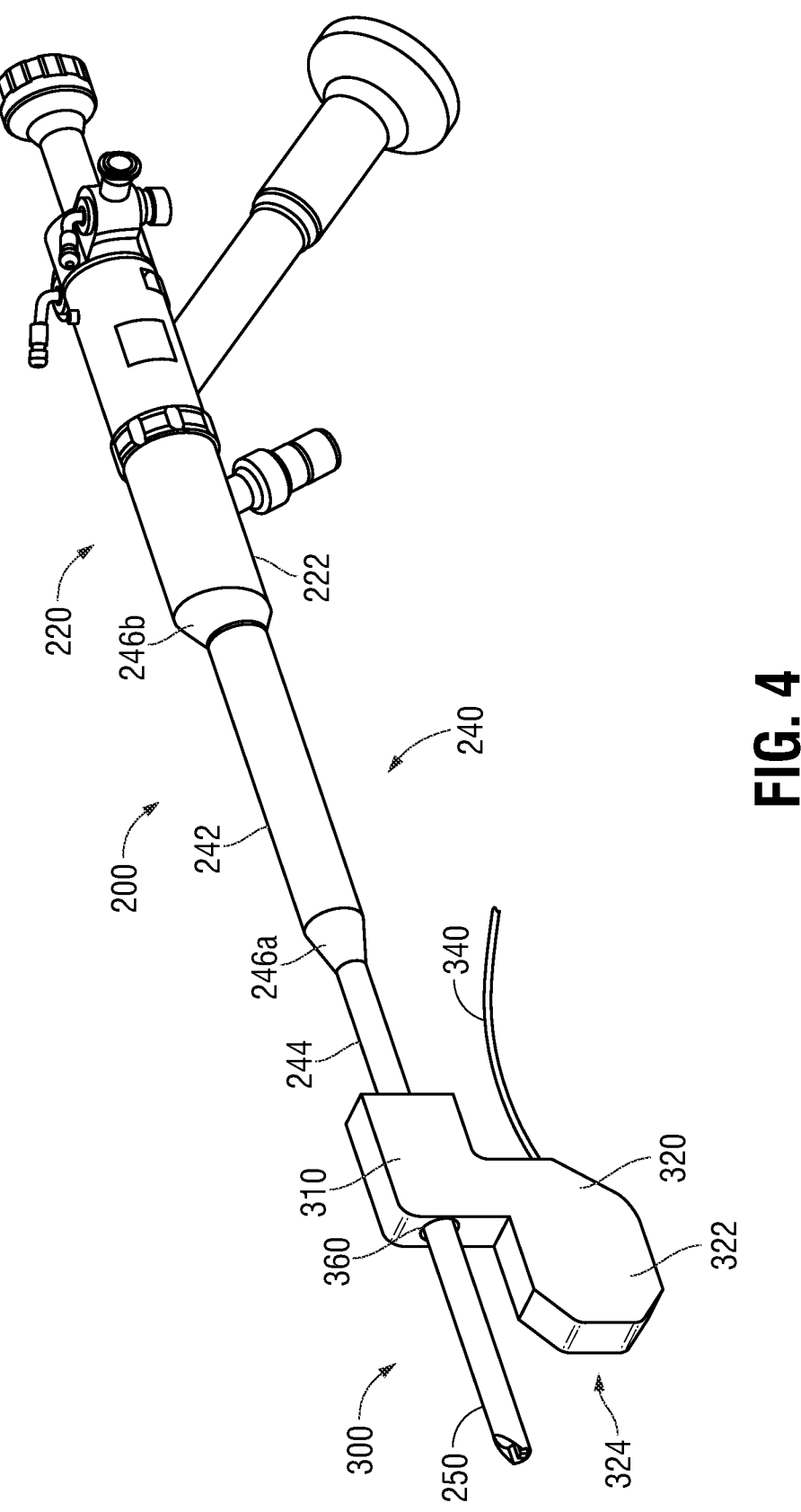
FIG. 4 is a perspective view illustrating the hysteroscope inserted through the ultrasound device.

Referring to FIGS. 3 and 4, ultrasound device 300 includes a collar 310, a body 320 extending from collar 310, an ultrasound sensor assembly 330 disposed within body 320, and a cable 340 configured to connect ultrasound sensor assembly 330 to an ultrasound console (not shown), e.g., via wires 350 extending from ultrasound sensor assembly 330 through body 320 and/or collar 310 and through cable 340. In aspects, ultrasound device 300 is configured for full insertion (with the exception of cable 340) transvaginally through the vaginal introitus and into the vaginal canal for positioning adjacent to or in contact with tissue surrounding the cervix. This configuration enables ultrasound imaging of the cervix, uterus, and/or surrounding tissue, while minimizing the overall diameter of instrumentation extending through the vaginal introitus (once ultrasound device 300 is passed through the vaginal introitus and into the vaginal canal).

Collar 310 of ultrasound device 300 defines a longitudinal lumen 360 extending through collar 310. Longitudinal lumen 360 is configured to permit passage of at least a portion of an endoscope device through collar 310. For example, longitudinal lumen 360 of collar 310 may be configured to receive distal portion 244 of shaft 240 of hysteroscope 200 therethrough. Longitudinal lumen 360 may additionally or alternatively be configured to permit passage of other instrumentation, e.g., one or more working devices, therethrough.

In aspects, longitudinal lumen 360 defines an internal diameter greater than the second, smaller diameter of distal portion 244 of shaft 240 but smaller than the first, larger diameter of proximal portion 242 of shaft 240. Thus, collar 310 of ultrasound device 300 is slidably positionable about distal portion 244 of shaft 240 of hysteroscope 200 (e.g., over distal tip 250 of shaft 240) but is inhibited from proximal sliding over first transition portion 246*a* of shaft 240 of hysteroscope 200 onto proximal portion 242 of shaft 240 of hysteroscope 200. In aspects, in addition to longitudinal sliding along distal portion 244 of shaft 240 of hysteroscope 200, collar 310 may be configured to rotate about distal portion 244 of shaft 240 of hysteroscope 200, e.g., about a longitudinal axis of hysteroscope 200.

Collar 310 defines a longitudinal length, in aspects, not greater than about 50% of a length of shaft 240 of hysteroscope 200; in other aspects, not greater than about 40% of a length of shaft 240 of hysteroscope 200; in still other aspects, not greater than about 30% of a length of shaft 240 of hysteroscope 200; or, in yet other aspects, not greater than about 20% of a length of shaft 240 of hysteroscope 200. In aspects, collar 310 defines a longitudinal length not greater than about 50% of a length of distal portion 244 of shaft 240 of hysteroscope 200; in other aspects, not greater than about 40% of a length of distal portion 244 of shaft 240 of hysteroscope 200; or, in still yet other aspects, not greater than about 30% of a length of distal portion 244 of shaft 240 of hysteroscope 200.

Continuing with reference to FIGS. 3 and 4, body 320 of ultrasound device 300 may be configured as a foot 322 depending from and protruding distally relative to collar 310 of ultrasound device 300. Thus, with shaft 240 of hysteroscope 200 extending through and distally from collar 310, foot 322 extends alongside a portion of shaft 240 of hysteroscope 200 that extends distally from collar 310. More specifically, foot 322 may be fixed relative to collar 310 and oriented such that foot 322 extends in substantially parallel orientation relative to shaft 240 of hysteroscope 200. Alternatively, foot 322 may be fixed relative to collar 310 and oriented such that foot 322 extends at an angle relative to collar 310 and thus, shaft 240 of hysteroscope 200. This angle, in aspects, may be from about 10 degrees to about 70 degrees, although other orientations and/or angles of foot 322 relative to collar 310 are also contemplated. Collar 310 and body 320, in aspects, may be integrally formed, e.g., methodically from a single piece of material. In other aspects, body 320 is configured to slide, pivot, and/or rotate relative to collar 310, thus permitting adjustment of the position and/or orientation of foot 322 relative to collar 310 and thus, shaft 240 of hysteroscope 200.

Foot 322 defines a curved (e.g., convex) distally-facing surface 324, thus providing an atraumatic interface for positioning distally-facing surface 324 of foot 322 in contact with tissue, e.g., positioning distally-facing surface 324 of foot 322 in contact with tissue surrounding the cervix (such as a vaginal fornix), to enable ultrasound sensor assembly 330 to image the cervix, uterus, and/or surrounding tissue.

Ultrasound sensor assembly 330 is disposed within body 320 of ultrasound device 300 and includes one or more ultrasound sensors 332, e.g., ultrasound transducers, oriented towards distally-facing surface 324 of foot 322 to emit ultrasound waves therefrom to enable ultrasound imaging of tissue, e.g., the cervix, uterus, and/or surrounding tissue. Each ultrasound sensor 332, more specifically, is configured to emit ultrasound waves, e.g., high-frequency sound waves, and to receive echoed waves produced by the reflection of the ultrasound waves against the various tissue structures encountered. The echoed waves received by each ultrasound sensor 332 are output to an image processing unit (not shown), e.g., by way of wires 360 extending through body 320 and cable 340. In aspects, ultrasound sensor assembly 330 includes one or more ultrasound sensors 332 configured for 2D ultrasound imaging. In other aspects, ultrasound sensor assembly 330 includes a plurality of ultrasound sensors 332 forming an ultrasound sensor array that defines a portion of a circle, a portion of a polygon, a partially-polygonal, partially-arcuate configuration, or other suitable configuration to enable reconstruction of a 3D ultrasound image therefrom for 3D ultrasound imaging.

Figure 5A:
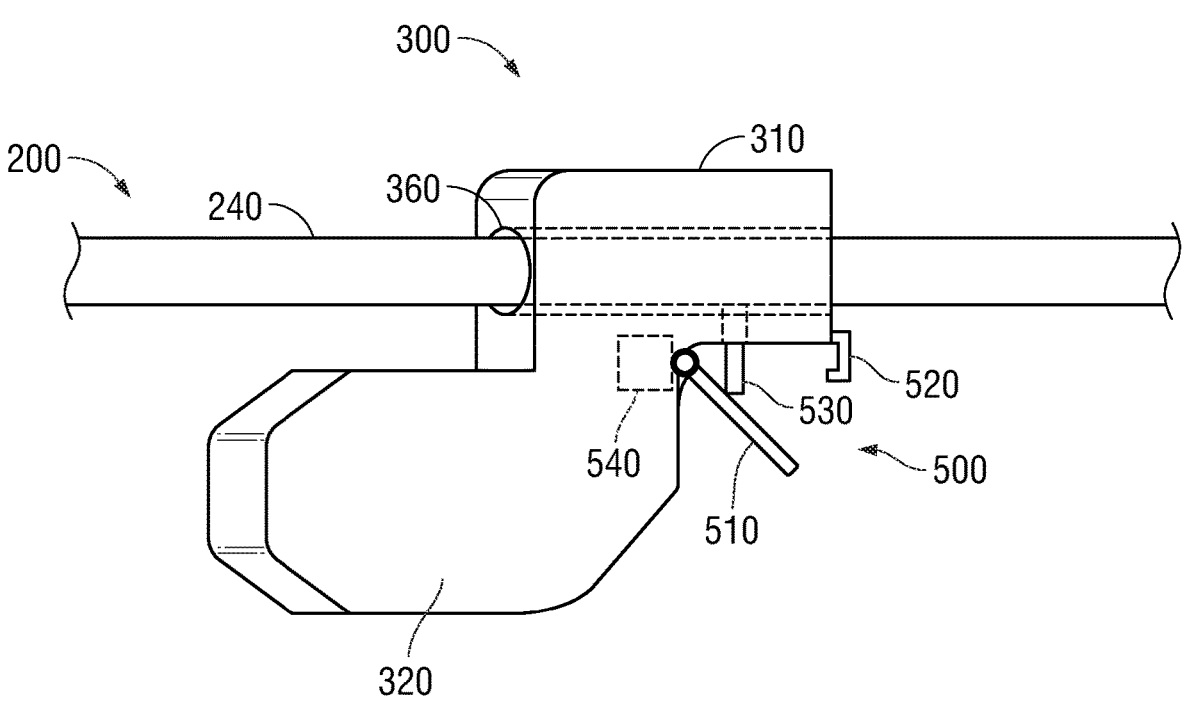
FIGS. 5A and 5B are perspective views of the ultrasound device disposed on the hysteroscope with a locking mechanism in unlocked and locked conditions, respectively.
Figure 5B:
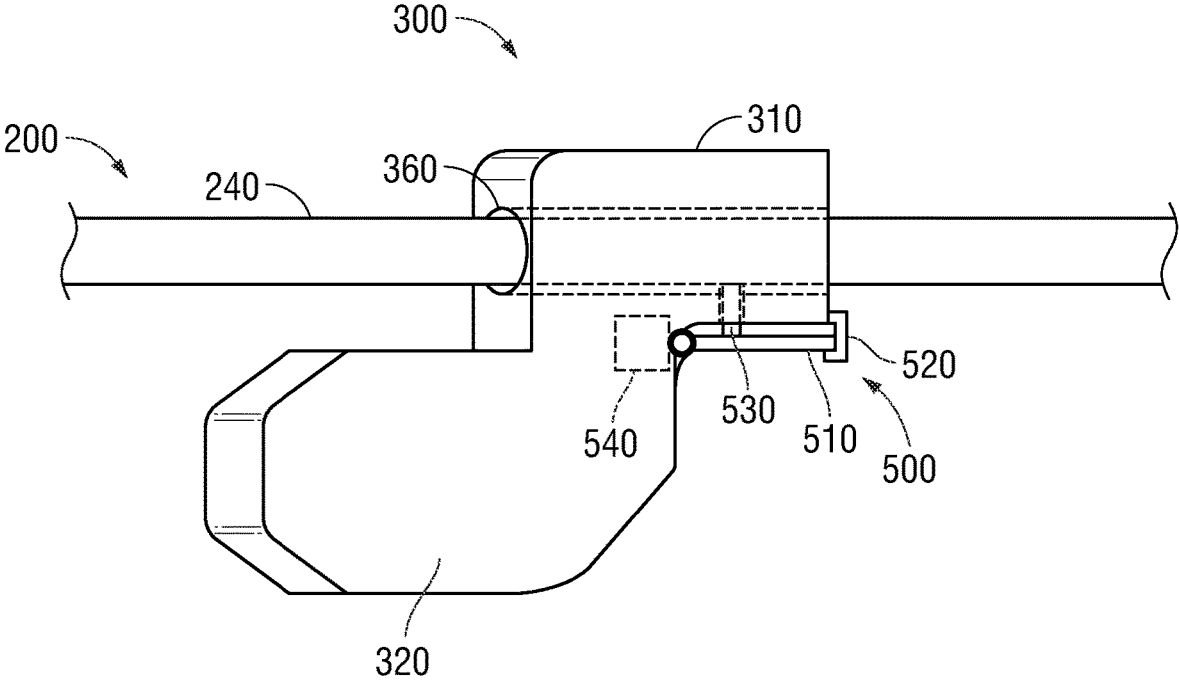

Referring to FIGS. 5A and 5B, in aspects, ultrasound device 300 includes a locking mechanism 500 configured to releasably engage collar 310 with shaft 240 of hysteroscope 200 to thereby translationally and/or rotationally fix collar 310 of ultrasound device 300 relative to shaft 240 of hysteroscope 200. Locking mechanism 500, more specifically, is transitionable between an unlocked condition (FIG. 5A), wherein collar 310 and shaft 240 are longitudinally slidable and/or axially rotatable relative to one another, and a locked condition (FIG. 5B), wherein collar 310 and shaft 240 are translationally and/or rotationally fixed relative to one another. Locking mechanism 500, as shown, includes a latch arm 510, a catch 520, and a lock pin 530. In the unlocked condition of locking mechanism 500, as shown in FIG. 5A, latch arm 510 is disengaged from catch 520 and lock pin 530 is displaced from longitudinal lumen 360 of collar 310, thus permitting longitudinal sliding and/or axial rotation of shaft 240 within longitudinal lumen 360 and relative to collar 310. In the locked condition of locking mechanism 500, as shown in FIG. 5B, latch arm 510 is engaged with catch 520, thereby urging lock pin 530 at least partially into longitudinal lumen 360 of collar 310 to clamp shaft 240 against an internal surface of longitudinal lumen 360, thus inhibiting longitudinal sliding and/or axial rotation of shaft 240 within longitudinal lumen 360 and relative to collar 310. Other suitable locking mechanisms are also contemplated.

In aspects, latch arm 510 is locally movable to transition locking mechanism 500 between the unlocked and locked conditions, e.g., via direct manipulation of latch arm 510. In other aspects, locking mechanism 500 includes a locking drive assembly 540 disposed on or within ultrasound device 300 and configured to move latch arm 510 to transition locking mechanism 500 between the unlocked and locked conditions. Locking drive assembly 540 may include mechanical drive components, e.g., gears, pulleys, cams etc., and/or electronic drive components, e.g., a motor. Locking drive assembly 540 may be configured for remote actuation via an electronic remote control (not shown) externally of the patient and wirelessly connected or wired (e.g., via wires extending through cable 340 (FIG. 3)) to locking drive assembly 540. Alternatively, locking drive assembly 540 may be configured for remote actuation via a mechanical actuator coupled to locking drive assembly 540 and extending through cable 340 (FIG. 3) for actuation externally of the patient.

Figures 6A, 6B, 6C:
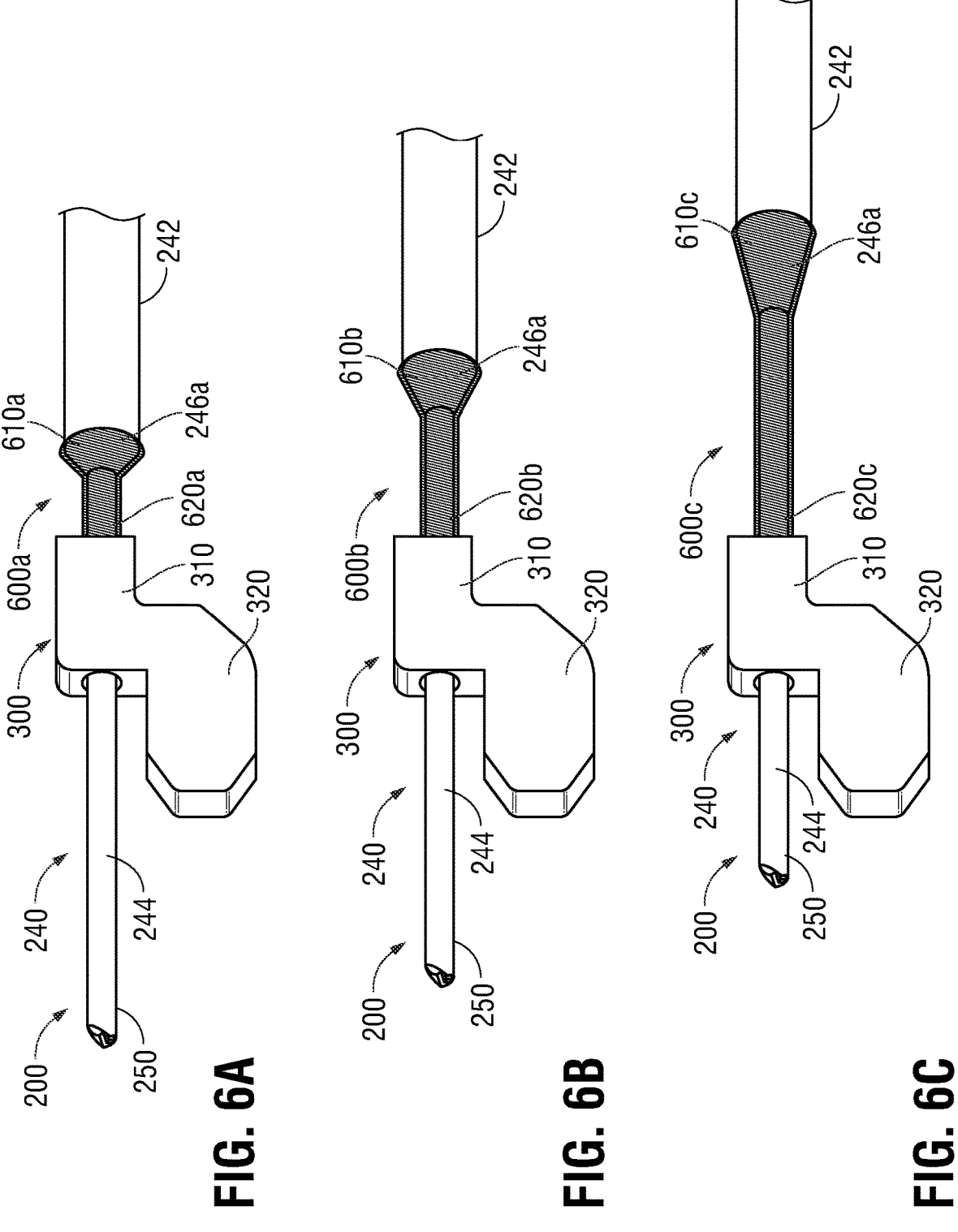
FIGS. 6A-6C are perspective views of the ultrasound device disposed on the hysteroscope with various different sized spacers positioning the ultrasound device relative to the hysteroscope.

Turning to FIGS. 6A-6C, as noted above, in aspects, collar 310 of ultrasound device 300 is slidably positionable about distal portion 244 of shaft 240 of hysteroscope 200 but is inhibited from proximal sliding over first transition portion 246a of shaft 240 of hysteroscope 200 onto proximal portion 242 of shaft 240 of hysteroscope 200. In these and other aspects, one or more spacers 600a, 600b, 600c (FIGS. 6A-6C, respectively) may be provided to limit the relative longitudinal motion between collar 310 of ultrasound device 300 and distal portion 244 of shaft 240 of hysteroscope 200. More specifically, rather than permitting shaft 240 of hysteroscope 200 to advance distally through collar 310 of ultrasound device 300 to a position wherein collar 310 is disposed at (or beyond) first transition portion 246a of shaft 240, spacers 600a, 600b, 600c are positionable about distal portion 244 of shaft 240 between first transition portion 246a and collar 310 to limit insertion of shaft 240 of hysteroscope 200 through collar 310, e.g., due to the abutment of collar 310 with a distal end 620a, 620b, 620c of the spacer 600a, 600b, 600c.

As shown in FIGS. 6A-6C, spacers 600a, 600b, 600c are disposed about distal portion 244 of shaft 240 and each includes a proximal end 610a, 610b, 610c configured to abut first transition portion 246a of shaft 240 and a distal end 620a, 620b, 620c. Spacer 600a defines a first length extending between proximal and distal ends 610a, 620a, respectively thereof; spacer 600b defines a second length, greater than the first length, extending between proximal and distal ends 610b, 620b, respectively; and spacer 600c defines a third length, greater than the second length, extending between proximal and distal ends 610c, 620c, respectively. Thus, distal tip 250 of shaft 240 of hysteroscope 200 is permitted to extend a first distance from collar 310 of ultrasound device 300 when spacer 600a is used; distal tip 250 of shaft 240 of hysteroscope 200 is permitted to extend a second distance, less than the first distance, from collar 310 of ultrasound device 300 when spacer 600b is used; and distal tip 250 of shaft 240 of hysteroscope 200 is permitted to extend a third distance, less than the second distance, from collar 310 of ultrasound device 300 when spacer 600c is used. Accordingly, with body 320 of ultrasound device 300 abutting tissue adjacent to or surrounding the cervix (and, thus, disposed in substantially fixed position relative to the patient's anatomy), and with an appropriate spacer 600a, 600b, 600c selected, the extent to which shaft 240 of hysteroscope 200 is insertable through the cervix and into the uterus can be set.

Figure 7A:
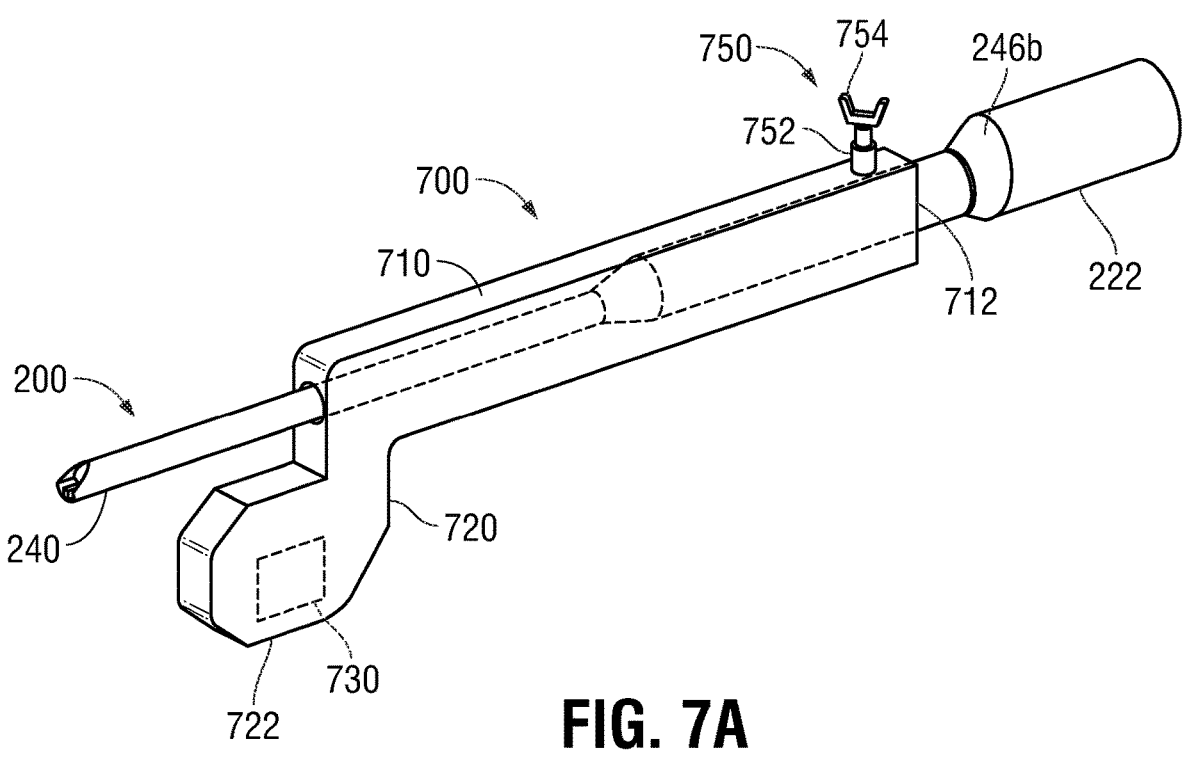
FIGS. 7A and 7B are perspective views of another ultrasound device provided in accordance with the present disclosure disposed on the hysteroscope with a locking mechanism in unlocked and locked conditions, respectively.
Figure 7B:
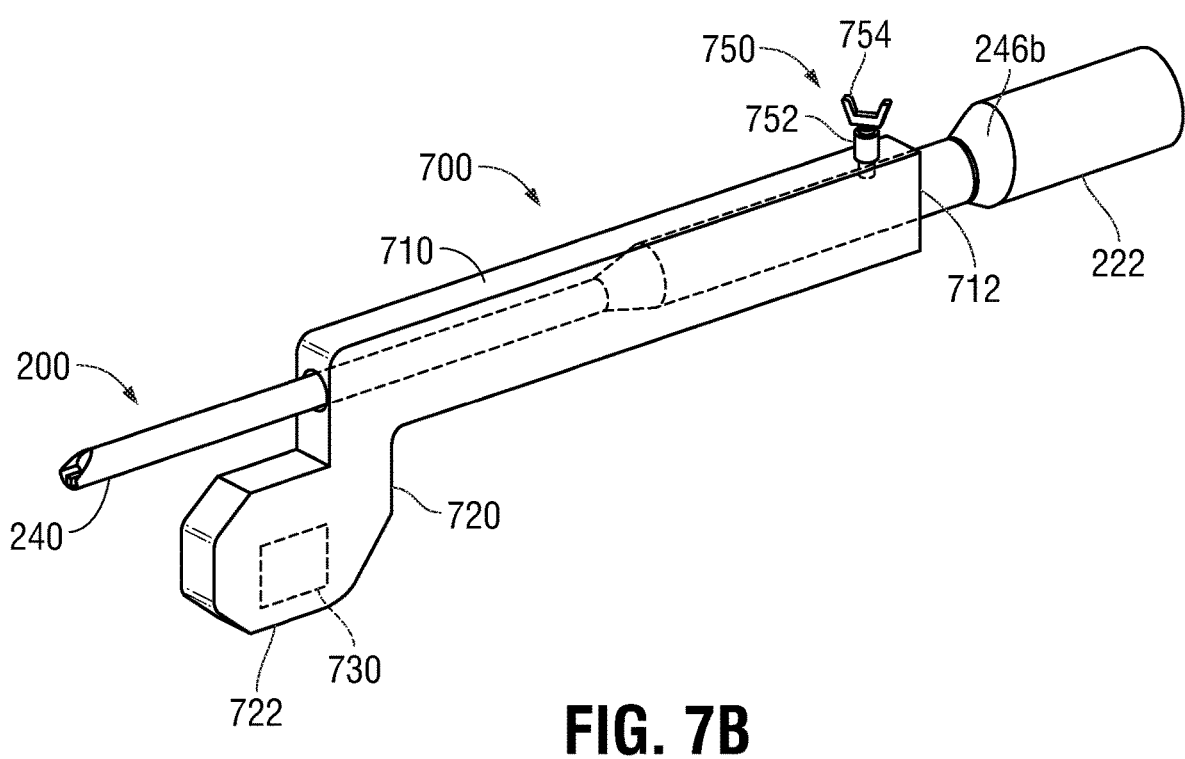

With reference to FIGS. 7A and 7B, another ultrasound device 700 provided in accordance with the present disclosure is shown. Ultrasound device 700 may be similar to and include any of the features of ultrasound device 300 (FIG. 3), except as explicitly contradicted below. As such, only differences between ultrasound device 700 and ultrasound device 300 (FIG. 3) are described in detail below while similarities are summarily described or omitted entirely.

Ultrasound device 700 includes a sleeve 710, a body 720 extending from sleeve 710, an ultrasound sensor assembly 730 disposed within body 720, and a cable (not shown) extending through or along sleeve 710 and configured to connect ultrasound sensor assembly 730 to an ultrasound console (not shown).

Sleeve 710 of ultrasound device 700 defines a longitudinal lumen extending therethrough that is configured to permit passage of at least a portion of an endoscope device through sleeve 710. For example, sleeve 710 may be configured to receive at least a portion of shaft 240 of hysteroscope 200.

Body 720 of ultrasound device 700 may be configured as a foot 722 depending from and protruding distally relative to sleeve 710 of ultrasound device 700. Foot 722 is configured for positioning in contact with tissue surrounding the cervix (such as a vaginal fornix), to enable ultrasound sensor assembly 730 to image the cervix, uterus, and/or surrounding tissue.

Sleeve 710 is configured such that, with foot 722 contacting tissue surrounding the cervix (such as a vaginal fornix), sleeve 710 extends proximally through the vaginal canal and vaginal introitus externally of the patient. Further, a proximal end 712 of sleeve may be configured to limit the relative longitudinal motion between sleeve 710 of ultrasound device 700 and shaft 240 of hysteroscope 200. More specifically, upon insertion of shaft 240 of hysteroscope 200 distally through sleeve 710, second transition portion 246b of shaft 240 of hysteroscope 200 contacts proximal end 712 of sleeve 710 and inhibits further distal advancement of shaft 240 of hysteroscope 200. Accordingly, with ultrasound device 700 abutting tissue adjacent to or surrounding the cervix (and, thus, disposed in substantially fixed position relative to the patient's anatomy), sleeve 710 defines the extent to which shaft 240 of hysteroscope 200 is insertable through the cervix and into the uterus. Sleeve 710, in aspects, is configured to telescope or is otherwise variable in length and/or different length sleeves 710 may be provided, thus enabling a selection of a sleeve 710 according to a desired amount of extension of shaft 240 of hysteroscope 200 through the cervix and into the uterus.

Continuing with reference to FIGS. 7A and 7B, in aspects, ultrasound device 700 further includes a locking mechanism 750 configured to releasably engage sleeve 710 with shaft 240 of hysteroscope 200 to thereby translationally and/or rotationally fix sleeve 710 of ultrasound device 700 relative to shaft 240 of hysteroscope 200. Locking mechanism 750 may include a threaded passage 752 and a threaded set screw 754 configured for threaded engagement with threaded passage 752. More specifically, rotation of threaded set screw 754 relative to threaded passage 752 in a first direction advances threaded set screw 754 radially inwardly and rotation of threaded set screw 754 in a second, opposite direction retracts threaded set screw 754 radially outwardly. Thus, threaded set screw 754 may be moved between a retracted position, corresponding to an unlocked condition (FIG. 7A), wherein shaft 240 is longitudinally slidable and/or axially rotatable relative to sleeve 710, and an inserted position, corresponding to a locked condition (FIG. 7B), wherein threaded set screw 754 clamps shaft 240 against an internal surface of sleeve 710, thus inhibiting longitudinal sliding and/or axial rotation of shaft 240 relative to sleeve 710. Other suitable locking mechanisms are also contemplated.

Figure 8A:
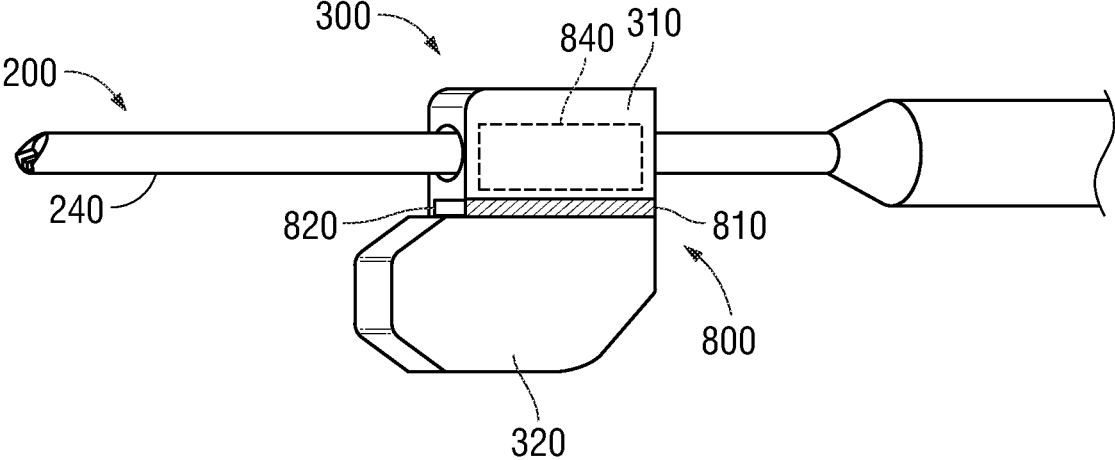
FIGS. 8A and 8B are perspective views illustrating longitudinal sliding of a first portion of the ultrasound device relative to a second portion of the ultrasound device and the hysteroscope.
Figure 8B:
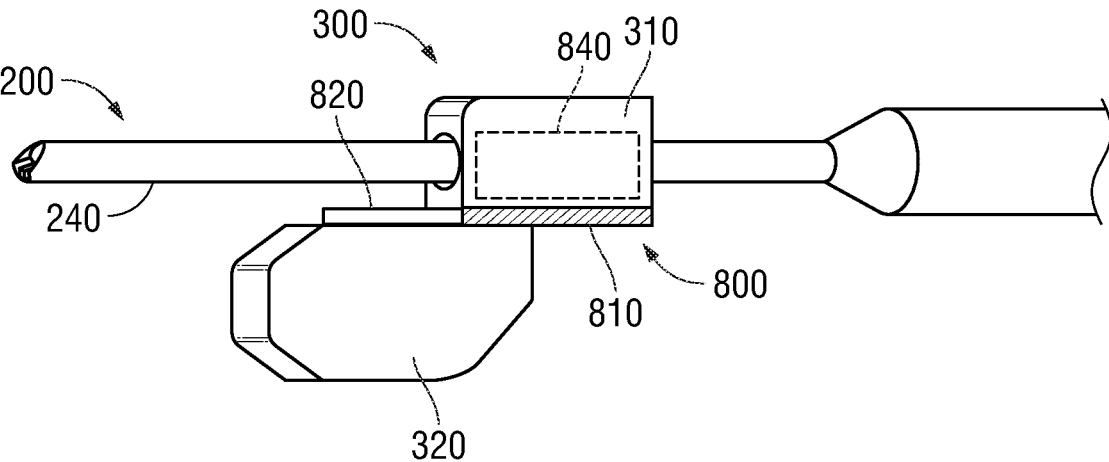
Figure 9A:
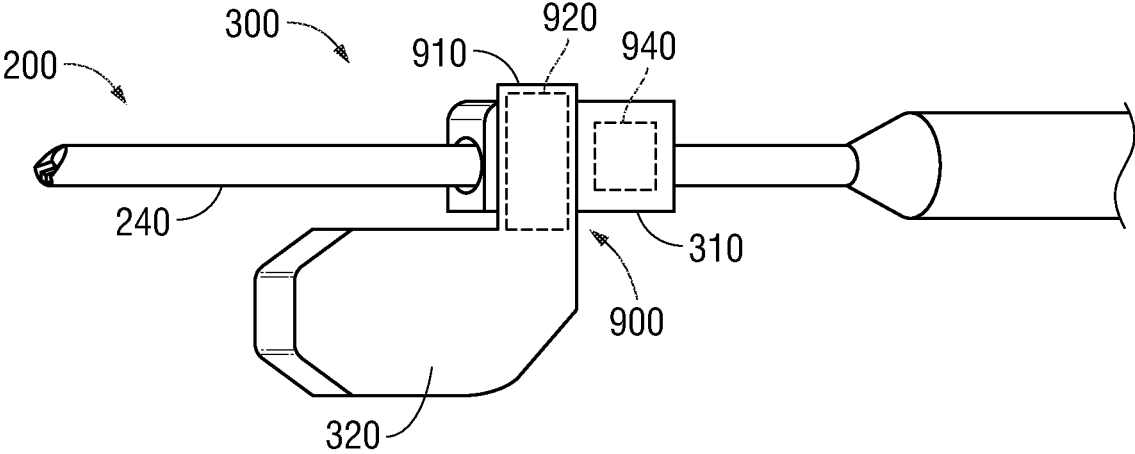
FIGS. 9A and 9B are perspective views illustrating axial rotation of a first portion of the ultrasound device relative to a second portion of the ultrasound device and the hysteroscope of about a longitudinal axis of the hysteroscope.
Figure 9B:
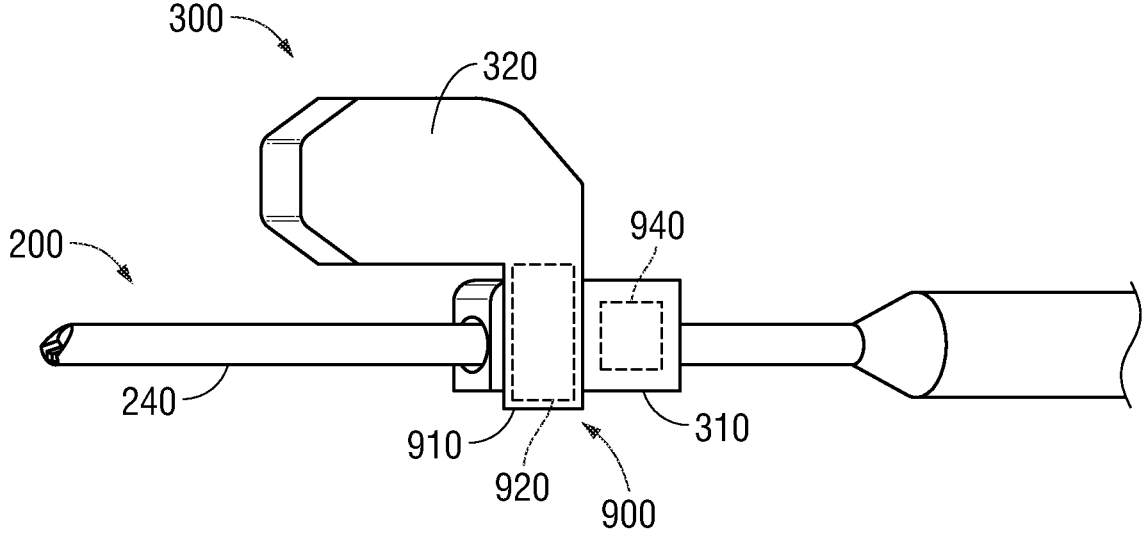
Figure 10A:
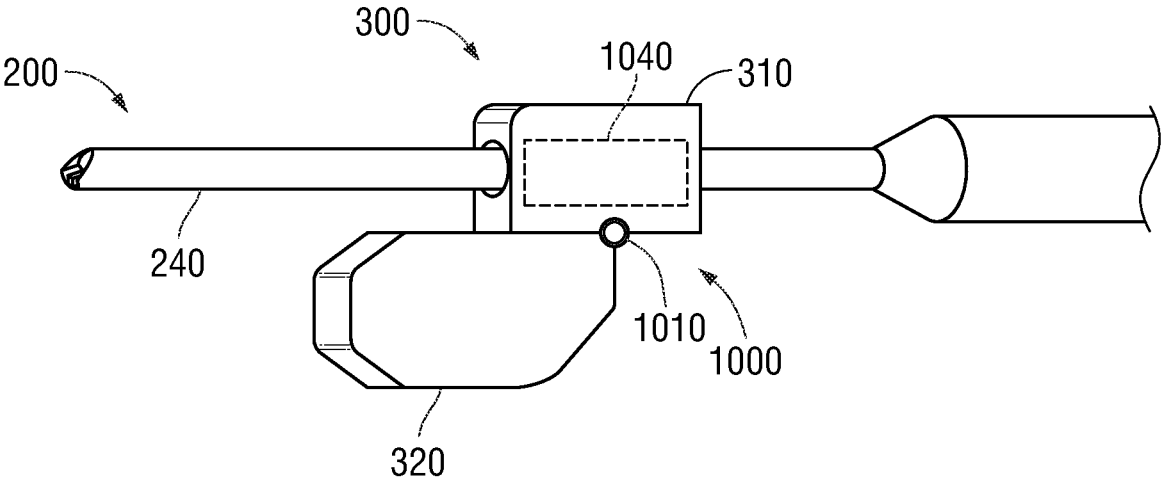
FIGS. 10A and 10B are perspective views illustrating pivoting of a first portion of the ultrasound device relative to a second portion of the ultrasound device and the hysteroscope to tilt the first portion relative to the second portion and the hysteroscope.
Figure 10B:
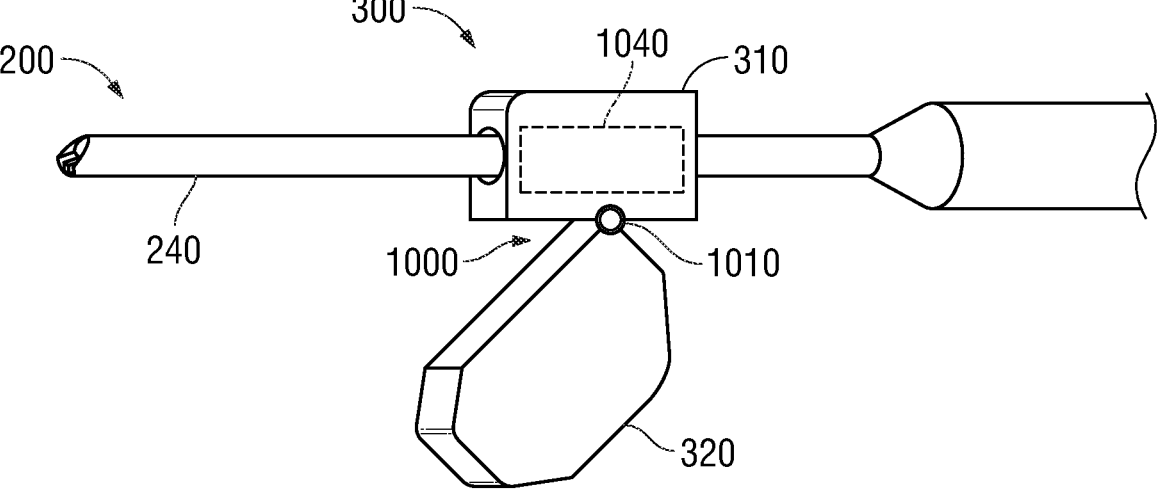

Turning to FIGS. 8A-10B, in addition to an entirety of ultrasound device 300 being longitudinally slidable along and/or axially rotatable about shaft 240 of hysteroscope 200 and, in aspects, lockable in longitudinal and/or rotational position about shaft 240 of hysteroscope 200, ultrasound device 300 may configured to enable relative motion between collar 310 and body 320. More specifically, as detailed below, body 320 may be configured to longitudinally translate relative to collar 310 (FIGS. 8A and 8B), rotate about collar 310 (FIGS. 9A and 9B), and/or pivot (or tilt) relative to collar 30 (FIGS. 10A and 10B).

Referring to FIGS. 8A and 8B, ultrasound device 300 may include a translation mechanism 800 configured to enable body 320 to longitudinally translate relative to collar 310. Translation mechanism 800 may include, for example a guide rail 810 disposed on one of collar 310 (as shown) or body 320 and a carriage 820 disposed on the other of collar 310 or body 320 (as shown). Carriage 820 is slidably engaged with guide rail 810 to enable translation of carriage 820 relative to guide rail 810 and, thus, translation of body 320 relative to collar 310 between, for example, a retracted position (FIG. 8A), wherein body 320 protrudes distally a relatively small distance relative to collar 310 (or does not protrude distally from collar 31), and an extended position (FIG. 8B) wherein body 320 protrudes distally a relatively large distance relative to collar 310. In aspects, translation mechanism 800 includes a discrete or continuous locking mechanism (not shown) to enable locking of body 320 relative to collar 310 at defined positions or at any suitable position, respectively.

Translation mechanism 800 may further include a drive assembly 840 including mechanical drive components, e.g., gears, pulleys, cams etc., and/or electronic drive components, e.g., a motor, for driving translation of body 320 relative to collar 310. Drive assembly 840 may be configured for remote actuation via an electronic remote control (not shown) externally of the patient and wirelessly connected or wired to drive assembly 840. Alternatively, drive assembly 840 may be configured for remote actuation via a mechanical actuator coupled to drive assembly 840 and extending outside of the patient for actuation externally of the patient.

As shown in FIGS. 9A and 9B, ultrasound device 300 may include a rotation mechanism 900 configured to enable body 320 to rotate about collar 310. Rotation mechanism 900 may include, for example, an extension 910 extending from body 320 and disposed about collar 310. Rotation mechanism 900 may further include a bearing 920 disposed between collar 310 and extension 910 to enable rotation of extension 910 and, thus, body 320 about a longitudinal axis of collar 310 (and/or a longitudinal axis of shaft 240 of hysteroscope 200). In aspects, rotation mechanism 900 includes a discrete or continuous locking mechanism (not shown) to enable locking of body 320 relative to collar 310 at defined positions or at any suitable position, respectively.

Rotation mechanism 900 may further include a drive assembly 940 including mechanical drive components, e.g., gears, pulleys, cams etc., and/or electronic drive components, e.g., a motor, for driving rotation of body 320 relative to collar 310. Drive assembly 940 may be configured for remote actuation via an electronic remote control (not shown) externally of the patient and wirelessly connected or wired to drive assembly 940. Alternatively, drive assembly 940 may be configured for remote actuation via a mechanical actuator coupled to drive assembly 940 and extending outside of the patient for actuation externally of the patient.

With reference to FIGS. 10A and 10B, ultrasound device 300 may include a pivot mechanism 1000 configured to enable body 320 to pivot (or tilt) relative to collar 310. Pivot mechanism 1000 may include, for example, a hinge 1010 pivotably coupling body 320 and collar 310 with one another. In aspects, pivot mechanism 1000 includes a discrete or continuous locking mechanism (not shown) to enable locking of body 320 relative to collar 310 at defined positions or at any suitable position, respectively.

Pivot mechanism 1000 may further include a drive assembly 1040 including mechanical drive components, e.g., gears, pulleys, cams etc., and/or electronic drive components, e.g., a motor, for driving pivoting of body 320 relative to collar 310. Drive assembly 1040 may be configured for remote actuation via an electronic remote control (not shown) externally of the patient and wirelessly connected or wired to drive assembly 1040. Alternatively, drive assembly 1040 may be configured for remote actuation via a mechanical actuator coupled to drive assembly 1040 and extending outside of the patient for actuation externally of the patient.

Figure 11:
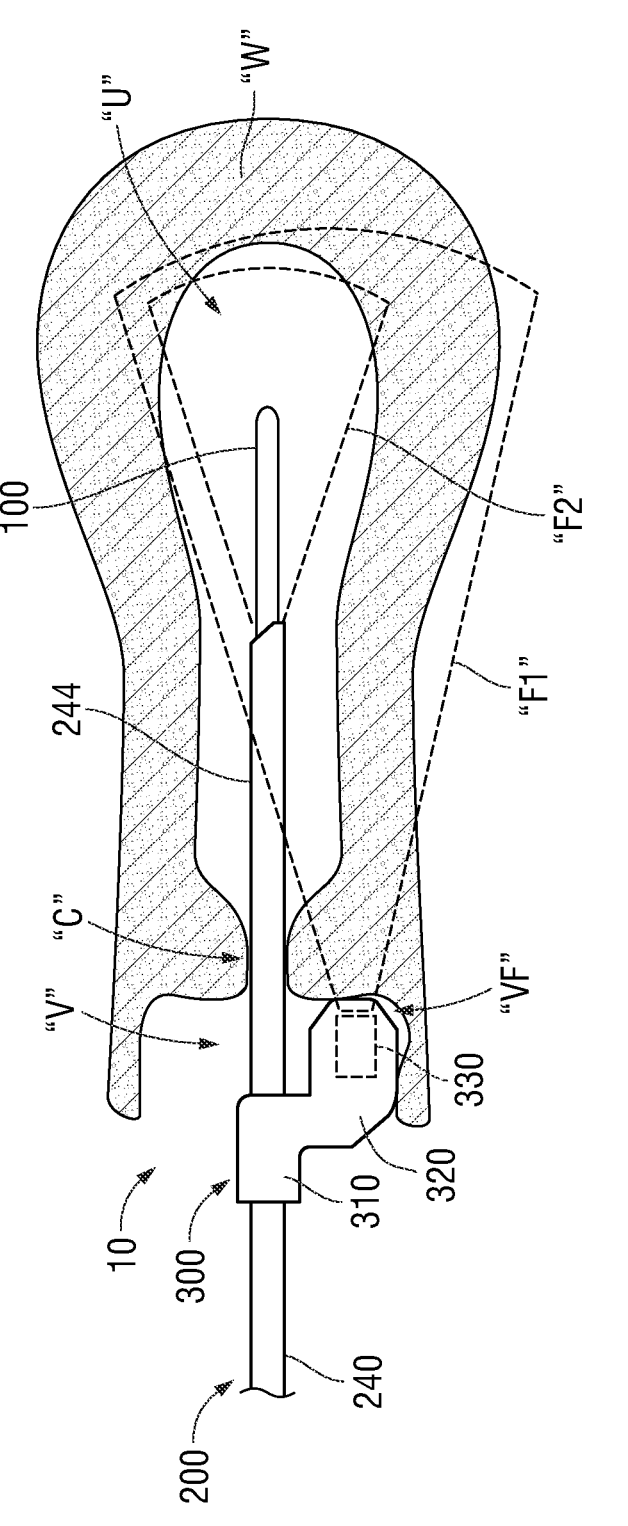
FIG. 11 is a side, partial cross-sectional view of the hysteroscopic system of FIG. 1 in use wherein the ultrasound device is positioned adjacent the cervix, the hysteroscope extends through the ultrasound device and through the cervix into the uterus, and the working device extends from the hysteroscope into the uterus.

Turning to FIG. 11, hysteroscopic system 10 is shown in use wherein ultrasound device 300 is inserted trans-vaginally through the vaginal introitus and into the vaginal canal "V" such that the entirety of ultrasound device 300 is disposed within the vaginal canal "V" with body 320, including ultrasound sensor assembly 330, positioned adjacent or in abutment with tissue surrounding the cervix "C," e.g., at a vaginal fornix "VF," to enable ultrasound imaging of a field of view "F1" including the uterus "U," uterine wall "W," and surrounding tissue. In this position, collar 310 is substantially aligned with the cervix "C." In aspects, ultrasound device 300 may be manipulated entirely or via movement of body 320 relative to collar 310, to achieve the above or other suitable positioning.

Continuing with reference to FIG. 11, distal portion 244 of shaft 240 of hysteroscope 200 extends through collar 310 of ultrasound device 300 through the cervix "C" and into the uterus "U." In this manner, hysteroscope 200 may be utilized for visualization within the uterus "U," e.g., providing a field of view "F2," together with or separately from the ultrasound imaging. Hysteroscope 200 may also be used for the introduction of fluid into and/or the removal of fluid from the uterus "U" and/or for passage of working device 100, e.g., a tissue resection device, ablation device, biopsy device, etc., therethrough and into the uterus "U" to perform one or more hysteroscopic tasks therein (e.g., within the uterus "U") or therethrough (e.g., within the uterine wall "W"). The use of ultrasound imaging of the uterus "U" from the exterior thereof and/or visualization of the uterus "U" from within the uterine cavity provides increased visibility for performing various different hysteroscopic tasks without the need to swap out instruments supporting different imaging modalities and/or providing different imaging perspectives.

Figure 12:
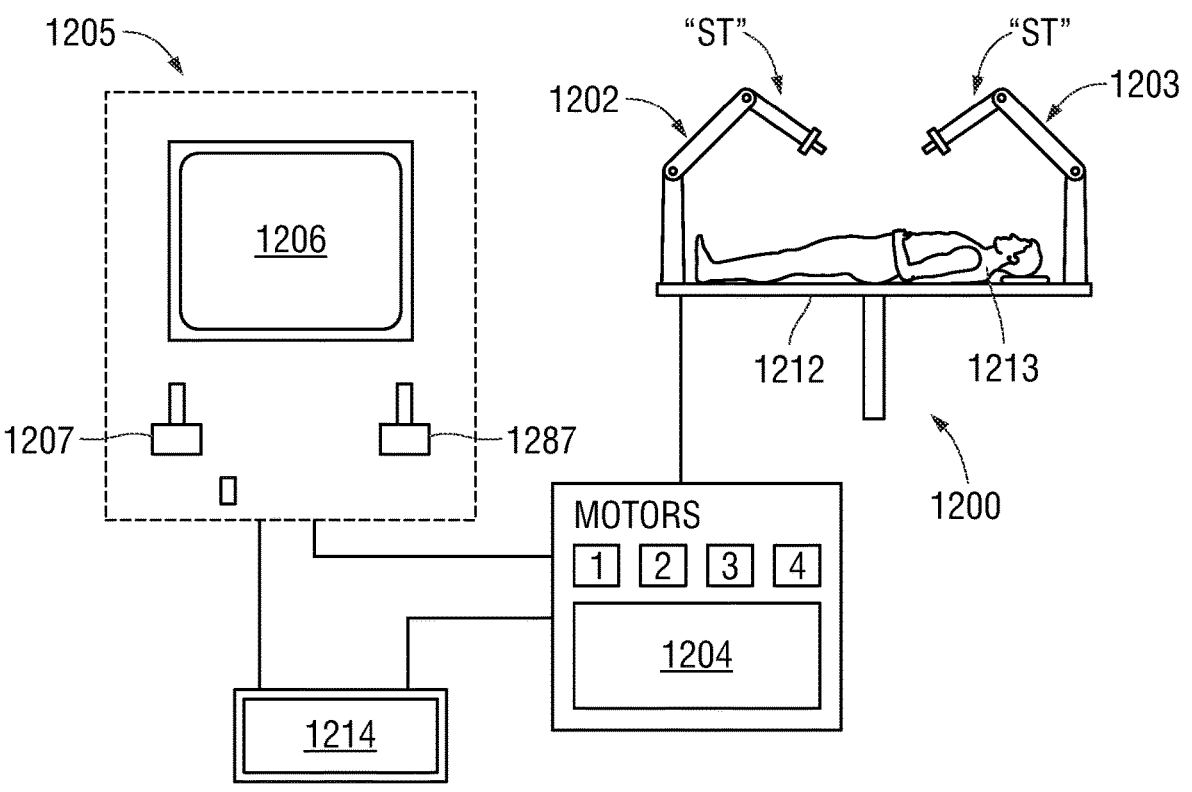
FIG. 12 is a schematic illustration of a robotic surgical system configured for use in accordance with the aspects of the present disclosure.

With reference to FIG. 12, a robotic surgical system 1200 configured for use in accordance with the present disclosure is shown. Aspects and features of robotic surgical system 1200 not germane to the understanding of the present disclosure are omitted to avoid obscuring the aspects and features of the present disclosure in unnecessary detail.

Robotic surgical system 1200 generally includes a plurality of robot arms 1202, 1203 (although two robot arms are shown, only one or more than two robot arms 1202, 1203 are also contemplated); a control device 12004; and an operating console 1205 coupled with control device 1204. Operating console 1205 may include a display device 1206, which may be set up in particular to display three-dimensional images; and manual input devices 1207, 1208, by means of which a person, e.g., a surgeon, may be able to telemanipulate robot arms 1202, 1203 in a first operating mode. Robotic surgical system 1200 may be configured for use on a patient 1213 lying on a patient table 1212. Robotic surgical system 1200 may further include a database 1214, in particular coupled to control device 1204, in which are stored, for example, pre-operative data from patient 1213 and/or anatomical atlases.

Each of the robot arms 1202, 1203 may include a plurality of members, which are connected through joints, and a mounted device which may be, for example, a surgical tool "ST." With momentary additional reference to FIG. 1, the surgical tools "ST" may include, for example, working device 100, hysteroscope 200, ultrasound device 300, etc., thus providing any of the above detailed functionality of system 10 on a robotic surgical system 1200.

Continuing with reference to FIG. 12, robot arms 1202, 1203 may be driven by electric drives, e.g., motors, connected to control device 1204. The motors, for example, may be rotational drive motors configured to provide rotational inputs to accomplish a desired task or tasks. Control device 1204, e.g., a computer, may be configured to activate the motors, in particular by means of a computer program, in such a way that robot arms 1202, 1203, and, thus, their mounted surgical tools "ST" execute a desired movement and/or function according to a corresponding input from manual input devices 1207, 1208, respectively. Control device 1204 may also be configured in such a way that it regulates the movement of robot arms 1202, 1203 and/or of the motors.

Control device 1204, more specifically, may control one or more of the motors based on rotation, e.g., controlling to rotational position using a rotational position encoder (or Hall effect sensors or other suitable rotational position detectors) associated with the motor to determine a degree of rotation output from the motor and, thus, the degree of rotational input provided. Alternatively or additionally, control device 1204 may control one or more of the motors based on torque, current, or in any other suitable manner.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular aspects. Those skilled in the art will envision other modifications within the scope and spirit of the claims appended hereto.

What is claimed is:

1. A transvaginal ultrasound device, comprising:
a collar defining a longitudinal lumen configured to receive a shaft for slidably positioning the collar about the shaft;
a body depending from the collar and protruding distally relative to the collar;
an ultrasound sensor assembly disposed within the body, the ultrasound sensor assembly configured for ultrasound imaging, wherein the collar and the body are configured for full insertion through a vaginal introitus and into a vaginal canal of a human patient for positioning the longitudinal lumen of the collar in substantial alignment with a cervix of the human patient to enable the shaft to extend through the cervix and into a uterus of the human patient; and
a drive assembly disposed within at least one of the collar or the body, the drive assembly configured to receive an actuation input and to drive movement of the body relative to the collar in response to receipt of the actuation input.

2. The transvaginal ultrasound device according to claim 1, further comprising a locking mechanism configured to releasably lock the collar about the shaft to at least one of slidably or rotationally fix the collar relative to the shaft.

3. The transvaginal ultrasound device according to claim 2, wherein the locking mechanism includes a locking drive assembly configured to transition the locking mechanism between a locked condition and an unlocked condition.

4. The transvaginal ultrasound device according to claim 1, wherein the movement of the body relative to the collar is rotational movement.

5. The transvaginal ultrasound device according to claim 1, wherein the movement of the body relative to the collar is slidable movement.

6. The transvaginal ultrasound device according to claim 1, wherein the movement of the body relative to the collar is pivotable movement.

7. A hysteroscopic surgical system, comprising:

a hysteroscope including a handle and a shaft extending distally from the handle; and an ultrasound device, including:

a collar defining a longitudinal lumen configured to receive the shaft for slidably positioning the collar about the shaft;

a body depending from the collar and protruding distally relative to the collar;

an ultrasound sensor assembly disposed within the body, the ultrasound sensor assembly configured for ultrasound imaging, wherein the collar and the body are configured for positioning within a vaginal canal of a human patient for positioning the longitudinal lumen of the collar in substantial alignment with a cervix of the human patient to enable the shaft to extend through the cervix and into a uterus of the human patient; and a drive assembly disposed within at least one of the collar or the body, the drive assembly configured to receive an actuation input and to drive movement of the body relative to the collar in response to receipt of the actuation input.

8. The hysteroscopic surgical system according to claim 7, wherein the shaft of the hysteroscope includes a first portion defining a first diameter and a second portion defining a second diameter greater than the first diameter, and wherein the longitudinal lumen of the collar defines a third diameter greater than the first diameter but less than the second diameter to enable slidable positioning the collar about the first portion of the shaft and inhibit sliding of the collar onto the second portion of the shaft.

9. The hysteroscopic surgical system according to claim 7, further comprising:

a spacer configured for positioning about the shaft of the hysteroscope proximally of the collar, the spacer configured to define an extent of distal insertion of the shaft of the hysteroscope through the collar.

10. The hysteroscopic surgical system according to claim 9, wherein the spacer is configured for positioning about the shaft of the hysteroscope between the collar and a transition defined along the shaft.

11. The hysteroscopic surgical system according to claim 7, further comprising a locking mechanism configured to releasably lock the collar about the shaft to at least one of slidably or rotationally fix the collar relative to the shaft.

12. The hysteroscopic surgical system according to claim 11, wherein the locking mechanism includes a locking drive assembly configured to transition the locking mechanism between a locked condition and an unlocked condition.

13. The hysteroscopic surgical system according to claim 7, wherein the movement of the body relative to the collar is rotational movement.

14. The hysteroscopic surgical system according to claim 7, wherein the movement of the body relative to the collar is slidable movement.

15. The hysteroscopic surgical system according to claim 7, wherein the movement of the body relative to the collar is pivotable movement.

16. The hysteroscopic surgical system according to claim 7, wherein the drive assembly includes a motor configured to drive movement of the body relative to the collar in response to receipt of the actuation input.

17. The hysteroscopic surgical system according to claim 7, wherein the actuation input is an electrical signal from a remote controller.

18. The transvaginal ultrasound device according to claim 1, wherein the drive assembly includes a motor configured to drive movement of the body relative to the collar in response to receipt of the actuation input.

19. The transvaginal ultrasound device according to claim 1, wherein the actuation input is an electrical signal from a remote controller.

20. The transvaginal ultrasound device according to claim 1, wherein the actuation input is a mechanical drive input from a remote mechanical actuator.

* * * * *